(12) United States Patent
Wagner et al.

(10) Patent No.: US 9,943,828 B2
(45) Date of Patent: Apr. 17, 2018

(54) HEAT EXCHANGE PROCESS FOR ADSORBER REGENERATION

(71) Applicant: BASF SE, Ludwigshafen (DE)

(72) Inventors: Hans-Guenter Wagner, Neuleiningen (DE); Christoph Bayer, Nuremberg (DE); Lothar Karrer, Pfungstadt (DE); Sven Crone, Limburgerhof (DE); Markus Eggersmann, Speyer (DE); Guenther Kirchner, Roemerberg (DE); Gabriele Zimmer, Karlsruhe (DE); Kam Wing Wong, Tsuen Wan (CN); Patrik Pietz, Shanghai (CN); Heinz Ruetter, Xanten (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/517,857

(22) PCT Filed: Oct. 9, 2014

(86) PCT No.: PCT/CN2014/088233
§ 371 (c)(1),
(2) Date: Apr. 7, 2017

(87) PCT Pub. No.: WO2016/054790
PCT Pub. Date: Apr. 14, 2016

(65) Prior Publication Data
US 2017/0252723 A1    Sep. 7, 2017

(51) Int. Cl.
| | | |
|---|---|---|
| *B01J 20/34* | (2006.01) | |
| *C07C 5/03* | (2006.01) | |
| *C07C 2/06* | (2006.01) | |
| *F28D 7/10* | (2006.01) | |
| *F28D 21/00* | (2006.01) | |

(52) U.S. Cl.
CPC ....... *B01J 20/3483* (2013.01); *B01J 20/3458* (2013.01); *C07C 2/06* (2013.01); *C07C 5/03* (2013.01); *F28D 7/10* (2013.01); *F28D 2021/0064* (2013.01)

(58) Field of Classification Search
CPC .... B01J 20/34; B01J 20/3483; B01J 20/3458; C07C 2/06; C07C 5/03; F28D 7/10
USPC ........................................................ 502/56
See application file for complete search history.

(56) References Cited

U.S. PATENT DOCUMENTS

| | | | |
|---|---|---|---|
| 4,935,399 A | 6/1990 | Blackburn et al. | |
| 4,935,400 A | 6/1990 | Blackburn et al. | |
| 5,177,298 A | 1/1993 | Yon et al. | |
| 6,334,316 B1 | 1/2002 | Maeda et al. | |
| 6,673,239 B2 | 1/2004 | Johnson et al. | |
| 2007/0123743 A1 | 5/2007 | Ng et al. | |
| 2011/0301398 A1 | 12/2011 | Heidemann et al. | |
| 2012/0024324 A1 | 2/2012 | Force et al. | |

FOREIGN PATENT DOCUMENTS

| | | |
|---|---|---|
| CN | 2905193 Y | 5/2007 |
| CN | 201404762 Y | 2/2010 |
| CN | 201543359 U | 8/2010 |
| CN | 102172461 A | 9/2011 |
| CN | 102430322 A | 5/2012 |
| CN | 103574791 A | 2/2014 |
| DE | 3 935 094 A1 | 4/1991 |
| DE | 10 2008 007 081 A1 | 8/2009 |
| WO | WO 99/47866 A1 | 9/1999 |
| WO | WO 01/83407 A1 | 11/2001 |
| WO | WO 2005/056503 A1 | 6/2005 |
| WO | WO 2010/057905 A1 | 5/2010 |

OTHER PUBLICATIONS

U.S. Appl. No. 15/517,558, filed Apr. 7, 2017, Hans-Guenter Wagner, et al.
U.S. Appl. No. 15/517,848, filed Apr. 7, 2017, Hans-Guenter Wagner, et al.
U.S. Appl. No. 15/517,682, filed Apr. 7, 2017, Hans-Guenter Wagner, et al.
U.S. Appl. No. 15/517,286, filed Apr. 6, 2017, Hans-Guenter Wagner.
U.S. Appl. No. 15/517,695, filed Apr. 7, 2017, Hans-Guenter Wagner, et al.
International Search Report and Written Opinion of the International Searching Authority dated Jul. 17, 2015 in PCT/CN2014/088233 filed Oct. 9, 2014.
International Preliminary Report on Patentability dated Feb. 8, 2017 in PCT/ CN2014/088233 filed Oct. 9, 2014.

*Primary Examiner* — Edward Johnson

(74) *Attorney, Agent, or Firm* — Oblon, McClelland, Maier & Neustadt, L.L.P.

(57) ABSTRACT

The invention relates to a process for regeneration of an adsorber (A) by contact with a stream (S1), wherein the stream (S1) is heated in advance by at least two heat exchange units (HEU1) and (HEU2). As outflow of the adsorber (A) a stream (S2) is obtained, which is passed through at least two heat exchange units (HEU1) and (HEU2) traversed by stream (S1), wherein the temperature of stream (S2) fed into each heat exchange unit is higher than the temperature of stream (S1) fed into the heat exchange units (HEU1) and (HEU2), in order to directly transfer heat from stream (S2) to stream (S1).

19 Claims, 1 Drawing Sheet

HEAT EXCHANGE PROCESS FOR ADSORBER REGENERATION

Figure 1:
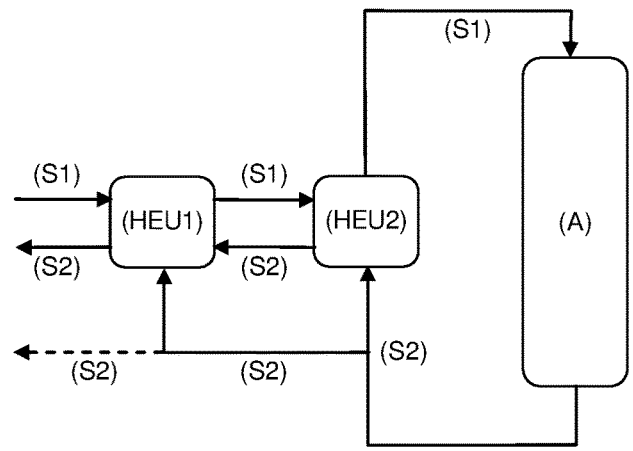

The invention relates to a process for the regeneration of an adsorber (A) by contact with a stream (S1), wherein the stream (S1) is heated in advance by at least two heat exchange units (HEU1) and (HEU2). As outflow of the adsorber (A) a stream (S2) is obtained, which is passed through at least two heat exchange units (HEU1) and (HEU2) traversed by stream (S1), wherein the temperature of stream (S2) fed into each heat exchange unit is higher than the temperature of stream (S1) fed into the heat exchange units (HEU1) and (HEU2), in order to directly transfer heat from stream (S2) to stream (S1).

Technical organic compositions often need to be purified from compounds containing heteroatoms in particular heteroatoms like sulfur or oxygen before use as starting materials in catalyzed reactions. These impurities may inhibit or lower the activities of catalysts. The purification can be performed by employing adsorbers.

WO 2010/057905 A1 discloses a process for the oligomerization of olefins by bringing at least one C2 to C8 olefin into contact with a nickel containing heterogeneous catalyst. Preferably the olefins are passed over an adsorption material before being brought in contact with the catalyst in order to prevent catalyst poisoning. However, WO 2010/057905 A1 does not disclose a process for heat recovery.

DE 10 2008 007 081 A1 discloses a process for the production of n-butene-oligomers and 1-butene from a technical mixture-I of $C_4$-hydrocarbons. Analogously to WO 2010/057905 A1, the document mentions the need for the removal of certain compounds containing heteroatoms out of the hydrocarbon mixture intended to be used in the catalyzed oligomerization process. The document does not disclose a process for heat recovery.

WO 2005/056503 discloses a composite catalyst for the selective oligomerization of lower alkenes and the production of high octane products. While the oligomerization of lower alkenes and mixtures of alkenes is reported in detail, a process for heat recovery is not mentioned.

WO 01/83407 describes a process for the oligomerization of alkenes having from 3 to 6 carbon atoms using a catalyst containing a zeolite of the MFS structure type under conditions to obtain selectively oligomeric product containing predominant amount of certain oligomers. Like in the previously discussed document of prior art a process for heat recovery is not part of the disclosure.

In order to remove the adsorbed compounds containing heteroatoms the regeneration of the adsorbers is required periodically. This can be achieved, for example, by purging the adsorber with inert gases or hydrocarbons at elevated temperatures. In order to raise the temperature of the regeneration media to the needed level, energy is consumed. Processes enabling efficient heat recovery from regeneration media, leaving the adsorber are therefore advantageous. Suitable regeneration media need to be essentially free of olefins and compounds containing heteroatoms, in particular free of compounds containing oxygen and/or sulphur. Residual olefins tend to form detrimental coke and polymer precipitates on the adsorbent, at the temperatures applied, during the regeneration process.

Technical organic compositions comprising olefins purified in an adsorber often comprise significant amounts of saturated hydrocarbons. These purified saturated hydrocarbons may be separated from the olefins in downstream process steps and would be applicable for the regeneration of the adsorbers. However, even after distillation of the product stream, the saturated hydrocarbon fraction usually still contains considerable amounts of residual olefins. Streams containing considerable amounts of olefins cannot successfully be employed for adsorber regeneration due to the increased formation of precipitates and/or coke on the adsorber surface.

U.S. Pat. No. 4,935,399 and U.S. Pat. No. 4,935,400 both describe a similar process for the reduction of hydrocarbon losses during regeneration of adsorbers containing molecular sieves for the removal of sulfur compounds from liquid hydrocarbon streams. While the process according to U.S. Pat. No. 4,935,399 comprises heating of the adsorber bed directly by a device located within the adsorber bed, in U.S. Pat. No. 4,935,400 the adsorber bed is heated by purging with gaseous hydrocarbon only. Both documents explain the use of hydrocarbon streams for the regeneration of adsorber beds containing molecular sieves, but none of them mentions heat recovery from the process streams.

U.S. Pat. No. 5,177,298 discloses a process for regeneration of oxygenate-containing adsorbents using hydrocarbon regenerant streams. The streams used require extra pretreatment by additional adsorbers in order to remove compounds containing sulfur or oxygen. Furthermore, U.S. Pat. No. 5,177,298 does neither disclose a process in which more than one heat recovery device is implemented nor a flexible process allowing efficient heat recovery at high and low temperatures.

U.S. Pat. No. 6,673,239 B2 discloses a system and process for removing water and compounds containing heteroatoms from hydrocarbons and a system and process for regeneration of adsorbents used therein. The regeneration comprises passing an isoparaffin over a water-adsorbent, then passing the isoparaffin over the heteroatom-containing compound adsorbent. However, a process for heat recovery is not mentioned in the disclosure.

US 2012/0024324 A1 discloses a process for regeneration of purification beds with a jet compressor in an open loop cycle. A fluid composition comprising an inert gas and a regeneration composition is used as regeneration media. Apart from hydrogen as possible secondary component, further constituents of the fluid composition are not defined. Furthermore, the document does not disclose a process for heat recovery using more than one heat recovery device for heat recovery from the same stream.

The problem underlying the present invention consists in the development of a new process for regeneration of an adsorber.

The object is achieved by a process for the regeneration of an adsorber (A) comprising the following steps a) to d):

a) heating of a stream (S1) in at least two heat exchange units (HEU1) and (HEU2), b) regeneration of an adsorber (A) by contact with the stream (S1) obtaining, as the outflow of the adsorber (A), a stream (S2), c) passing the stream (S2) through the heat exchange unit (HEU2), wherein the temperature of stream (S2) fed into the heat exchange unit (HEU2) is higher than the temperature of stream (S1) fed into the heat exchange unit (HEU2) in order to transfer heat from stream (S2) to stream (S1), d) passing the stream (S2) through the heat exchange unit (HEU1), wherein the temperature of stream (S2) fed into the heat exchange unit (HEU1) is higher than the temperature of the stream (S1) fed into the heat exchange unit (HEU1) in order to transfer heat from stream (S2) to stream (S1), wherein i) step c) and d) may be run in parallel by splitting stream (S2) into two parts, ii) step c) is followed by step d) and the temperature of stream (S2) fed into the heat exchange unit (HEU2) is higher or equal than its temperature when being fed into heat exchange unit (HEU1) and/or iii) temporarily only one of the steps c) and d) is carried out.

The process according to the present invention using at least two heat exchange units allows efficient recovery of heat from a process stream (S2) for transfer to another stream (S1) in a process for regeneration of an adsorber and consequently cooling of a process stream (S2) at the same time.

Varying target temperatures for stream (S1) can be obtained at varying temperatures of stream (S2) with no mutual constraint concerning the introduction of heat by conventional heat sources and by the heat exchange units used for heat recovery from stream (S2) at certain temperature ranges. This effect is of particular importance in adsorber regeneration, since the required target temperatures for the regeneration media are transient.

Alternative, more obvious solutions using only one heat exchange unit to recover heat from stream (S2), not according to the present invention, show less flexibility and less efficient heat recovery properties at varying temperatures of stream (S1) and (S2).

For example, if stream (S1) is passed through a heat exchange unit first, followed by a steam heater, the steam-heater is useless, if the recovered heat raises the temperature of the stream (S1) above the temperature of the steam. The heat required to reach the target temperature of stream (S1) would have to be provided instead by an electric heater, resulting in consumption of additional electric energy. Consequently, this process, in contrast to the present invention, would not be efficient at high temperature ranges.

However, if a process is applied, in which the heat integration unit and the steam-heater can be passed according to the previous example or vice versa, the heat recovery is not limited at higher temperature ranges anymore. Although, it is limited by the temperature of stream (S1) leaving the steam-heater, or in other words, it is limited at lower temperature ranges. Further, the flow of stream (S1) and (S2) in the heat integration unit is co-current in case of simple pipe routings, thus limiting heat exchange.

These alternative solutions in comparison with the present invention show that the careful selection of conventional and heat recovery based evaporation and heating devices, as well as the actual stream routing lay-out are crucial for efficient heat recovery and cooling of streams with varying temperatures.

When at least two heat exchange units are applied for heat recovery from stream (S2), heat recovery in the present invention is not limited at low or high temperatures of the streams (S1) or (S2), since one heat exchange unit may be used to recover heat from stream (S2) at high temperatures and another at lower temperatures.

In one embodiment, one heat exchange unit is applied for recovering heat from stream (S2) for evaporation of stream (S1), while another transfers heat from stream (S2) for super-heating of stream (S1). Consequently, at times when the temperature of stream (S2) is too low for super-heating stream (S1), remaining heat in stream (S2) is not lost, but can be still used advantageously for evaporation of stream (S1).

In another embodiment of the invention, the stream (S1) can be obtained by hydrogenation of a stream (S0) comprising alkanes and olefins and subsequently be applied for adsorber regeneration, without significant formation of detrimental precipitates of coke and polymers on the adsorbent. This is of significant importance, in particular in combination with another embodiment of the invention, as explained in the next paragraph.

In a further embodiment of the present invention, the stream (S1) originates from an earlier process step. Thus, the present invention allows the employment of components as regeneration media for an adsorber whereby said components have been purified earlier on the same adsorber, but who are in fact by-products, for example, within a process for producing octene by dimerization of butene. Such by-products are usually discharged as waste, but within the process of the present invention they can be successfully employed/converted into a regeneration stream.

Compared to other processes of prior art, when the process of the present invention is applied on the regeneration of adsorbers, no additional purification step to remove compounds containing sulfur and/or oxygen and/or other heteroatoms is required since these hydrocarbon mixtures are obtained for example as side products during purification of technical organic compositions comprising olefins by means of adsorbers. The purchase of alternative regeneration media like inert gases is therefore avoided.

Furthermore, another advantage of the present invention can be seen in the fact that one embodiment of the invention allows the operation of at least one adsorber in regeneration mode parallel to the operation of at least one other adsorber in operation mode in the same plant.

In order to enrich the regeneration media as much as possible with adsorbed compounds containing heteroatoms and consequently consuming regeneration media in an amount as low as possible, the flow of the regeneration media can be directed opposite to the flow of any organic composition in the operation mode of the adsorber.

For cooling of the adsorber the regeneration media can be passed through the adsorber according to the direction of the flow of any organic composition during the operation mode taking full advantage of the temperature gradient within the adsorber, further lowering the consumption of regeneration media.

In summary, operating costs and environmental burden are lowered by reduction of energy consumption, waste and recycling due to a combination of advantageous measures implemented in the present invention. Furthermore, the present invention provides a method for efficient regeneration of adsorbers.

The invention is specified in more detail as follows:

The present invention relates to a process for the regeneration of an adsorber (A) comprising the following steps a) to d):

Within the context of the present invention, the term "adsorber" comprises the adsorbent as well as the device in which the adsorbent is embedded in. Instead of the term "adsorbent" the expression "adsorber material" may be used. The term adsorber may be used equivalently for adsorbent, even if a certain statement actually refers only to the adsorbent but not to the device in which the adsorbent is embedded in.

The absorber (A) can be employed for the adsorption of compounds containing oxygen and/or sulphur out of organic compositions. Preferably, the adsorber (A) can be employed for the adsorption of ethers, alcohols, thiols, thioethers, sulfoxides, ketones, aldehydes or mixtures thereof.

Any adsorbent known to the person skilled in the art being appropriate for performing the adsorption of compounds containing oxygen and/or sulphur out of organic compositions may be applied.

Preferred adsorbents are, for example, molecular sieves with a pore diameter of 4 to 15 Å. Further, molecular sieves applicable are crystalline, natural aluminia silicates, like layer lattice silicates or synthetic molecular sieves. Furthermore, commercially available molecular sieves as sold by the Bayer AG, Dow, Union Carbide, Laporte or Mobil may be used. These molecular sieves can be, for example, zeolithes of the A-, X, and Y-type. Moreover, synthetic molecular sieves comprise silicium and aluminium as main components, whereby other atoms as side-components such as lanthanides like gallium, indium and lanthanum or other elements like nickel, cobalt, copper, zinc or silver may be useful. These can be introduced into the zeolithe for example by means of an ion-exchange with exchangeable cations.

Likewise, synthetic zeolithes can be employed, in which other atoms like boron or phosphorus are incorporated in the layer by co-precipitation.

Further suitable adsorbents are aluminium phosphate, silicium dioxide, kieselgur, titanium dioxide, zirconium dioxide, polymeric adsorbents and mixtures thereof.

The most preferred adsorbent is aluminium oxide, commercially available for example as Selexsorb CDL from BASF.

Preferably the adsorber (A) is based on aluminium oxide and/or the adsorber (A) can be employed for the adsorption of compounds containing oxygen and/or sulphur out of organic compositions, preferably the adsorber (A) can be employed for the adsorption of ethers, alcohols, thiols, thioethers, sulfoxides, ketones, aldehydes or mixtures thereof.

Regeneration, in the context of the present invention, means desorption and removal of adsorbed compounds containing oxygen and/or sulfur from the adsorber (A), in particular from the adsorbent in the adsorber (A). The inventive process for regeneration of the adsorber (A) may also comprise additional measures/steps necessary, for example, for preparation of the regeneration medium, the adsorber (A) itself for regeneration or for enabling the adsorber (A) after finished regeneration to be operated again for adsorption of compounds containing oxygen and/or sulphur out of organic compositions.

Consequently, an adsorber, within this invention, can at least be operated in the modes of operation: operation mode or regeneration mode.

An adsorber, within this invention, is in operation mode, when a stream comprising an organic composition, comprising at least one alkane and/or at least one olefin and compounds containing oxygen and/or sulphur, preferably not being routed through the adsorber before, is fed into the adsorber and compounds containing oxygen and/or sulphur are adsorbed completely or at least partially from this stream on the adsorbent.

Preferably at least 50%, more preferably at least 80%, most preferably at least 97% of the compounds containing oxygen and/or sulphur are adsorbed from the stream comprising organic composition according to the preceding paragraph.

An adsorber, within this invention, is in regeneration mode when measures to remove or measures related to the removal of adsorbed compounds containing oxygen and/or sulphur from the adsorbent are carried out or optionally the definition of the operation mode does not apply.

The steps a), b), c) and d) within the process for regeneration of an adsorber according to the present invention are defined as follows:

In step a) stream (S1) is heated in at least two heat exchange units (HEU1) and (HEU2).

Stream (S1)

i) may comprise at least 99 wt-% of at least one alkane, preferably at least 99.5 wt-% of at least one alkane, most preferably at least 99.9 wt-% of at least one alkane, preferably the alkane is butane, and/or ii) may comprise not more than 1000 wt-ppm olefin, preferably not more than 500 wt-ppm olefin, most preferably not more than 100 wt-ppm olefin, preferably the olefin is butane.

Preferably the alkane contains 1 to 14, more preferably 3 to 10, most preferably 4 to 6 carbon atoms in its longest chain.

The at least one alkane can be, for example, linear, branched and/or cyclic and is selected from the group: methane, ethane, propane, butane, pentane, hexane, heptane, octane, nonane and decane. Preferably the at least one alkane is butane.

In the context of the present invention, if not stated otherwise, it is not differentiated between the different isomers of a certain alkane. For example, the term butane may refer to n-butane and/or isobutane.

The olefin in stream (S1), stream (S2) and stream (S0) ((S2) and (S0) as defined below) may comprise at least one linear, branched, cyclic monoolefin and/or at least one linear, branched, cyclic olefin containing more than one olefinic double bond. Preferably the olefin has 2 to 14, more preferably 3 to 10, most preferably 4 to 6 carbon atoms in its longest carbon chain.

If more than one stereoisomer of an olefin exists, e.g. the corresponding cis- and trans-isomer, these isomers are, in the context of the present invention, regarded as equivalent. Further, it is not differentiated between constitutional isomers of monoolefins. For example, the term butene may comprise the constitutional isomers 1-butene and/or 2-butene as well as 2-butene the corresponding cis- and/or trans-stereoisomer.

Monoolefins can be, for example, selected from the group: ethene, propene, butene pentene, hexene, heptene, octene, nonene and decene. Preferably, the olefin is butene.

If at least one olefin containing more than one olefinic double bond is present, this olefin is preferably a diene, more preferably butadiene.

Heat exchange units as such are known to a person skilled in the art. At least one of the heat exchange units (HEU1) and (HEU2) and/or any further heat exchange unit employed in the process may preferably be an evaporator based on heat recovery or a super-heater based on heat recovery.

Within the present invention, an evaporator is a device which converts a stream from the liquid phase into gaseous phase by transfer of heat to the liquid stream.

Any evaporator known to the person skilled in the art, based on heat recovery, able to transfer heat from stream (S2) (as defined below) to stream (S1) may be employed as heat exchange unit (HEU1) and/or (HEU2).

Preferably, the evaporators used as heat exchange unit (HEU1) and/or (HEU2) are of the shell-and-tube type and/or of the Kettle type.

Super-heating, in the context of the present invention, means further increasing the temperature of the already gaseous stream (S1), preferably by transfer of heat from the gaseous stream (S2).

Any super-heater known to the person skilled in the art, based on heat recovery, able to transfer heat from stream (S2) (as defined below) to stream (S1) may be employed as heat exchange unit (HEU1) and/or (HEU2).

Preferably, super-heaters used as heat exchange unit (HEU1) and/or (HEU2) are tube bundle heat exchangers.

Dependent on the temperature actually required at a given time of the process, the heat transfer to the liquid or gaseous stream (S1) by the respective evaporators and/or super-heaters, including the further evaporators/super-heaters as defined below, may be reduced, stopped completely and/or one or any number of evaporators and/or one or any number of super-heaters may be by-passed by stream (S1).

Preferably gaseous stream (S1) is passed through heat exchange unit (HEU1) and/or (HEU2) and heat transfer is reduced or stopped when lower temperatures for gaseous stream (S1) are required.

Preferably heat exchange unit (HEU1) and/or (HEU2) are by-passed if liquid stream (S1) is required.

Besides evaporators and/or super-heaters based on heat recovery which may be used as heat exchange unit (HEU1) or (HEU2), further evaporators and/or super-heaters, in which heat is transferred to stream (S1) from other media than stream (S2) or other heat sources, may be employed.

Such media may be, for example, steam (gaseous water) or other gaseous media, hydrocarbons, oils or salts.

The same type of heat transfer medium can be applied for all further evaporators and/or super-heaters or different types of heat transfer media for each individual device or a group of evaporators and/or super-heaters may be used.

Another heat source may be electric energy. Consequently these further evaporators and/or super-heaters may be electric evaporators and/or electric super-heaters.

Evaporation and super-heating may be performed in different devices and/or be combined in at least one device capable to fulfill both functions, for instance a shell-and-tube heat exchanger stacked on top of a Kettle-type evaporator.

Stream (S1) may flow in series and/or in parallel through the evaporators and/or super-heaters employed.

In one further embodiment the process according to the present invention comprises at least one, preferably all of the options i) to v) as follows:
 i) at least one evaporator is a Kettle-evaporator or a shell-and-tube evaporator and/or
 ii) at least one super-heater is a tube bundle heat exchanger and/or
 iii) stream (S1) is passed in step a) through at least one super-heater (SH1), preferably operated with steam, prior to being passed through heat exchange unit (HEU2), and/or
 iv) stream (S1) is passed in step a) through at least one evaporator, preferably operated with steam, prior to being passed through heat exchange unit (HEU2), and/or
 v) stream (S1) is passed in step a) through at least one further super-heater, preferably an electric super-heater, after passing heat exchange unit (HEU2).

Step a) may comprise at least one of the component steps a1) to a6):
 a1) feeding a liquid stream (S1) into a flash vessel (FV) to obtain gaseous stream (S1) and liquid stream (S1);
 a2) superheating gaseous stream (S1), optionally obtained in any of component steps a1), a3), a4), a5) and/or a6), in a super-heater (SH1), preferably a steam-based super-heater;
 a3) superheating gaseous stream (S1), optionally obtained in any of component steps a1), a2), a4), a5) and/or a6), in a heat exchange unit (HEU2), which is a super-heater, wherein heat is recovered from stream (S2);
 a4) super heating gaseous stream (S1), optionally obtained in any of component steps a1), a2), a3), a5) and/or a6), in a further super-heater (H), preferably an electric heater;
 a5) converting liquid stream (S1), optionally obtained in component step a1), in a heat exchange unit (HEU1), which is an evaporator, wherein heat is recovered from stream (S2), into gaseous stream (S1) used in any of steps a2), a3) and/or a4);
 a6) converting liquid stream (S1), optionally remained from step a5), in an evaporator (E), preferably a steam-based evaporator, into gaseous stream (S1) and gaseous stream (S1) obtained is used in any of the steps a2), a3), and/or a4);
  preferably step a) comprises all component steps a1) to a6),
  preferably all optional relations are non-optional and/or
  preferably the steps a2), a3) and a4) are conducted in the order a2), followed by a3), followed by a4).

In component step a1) a liquid stream (S1), originating for example from step e), with a pressure of 5 to 80 bar, preferably of 10 to 50 bar, most preferably of 20 to 30 bar is fed into a flash vessel, wherein the pressure of liquid stream (S1) is lowered to 4 to 16 bar, preferably to 7 to 13 bar, most preferably to 8 to 11 bar.

Lowering the pressure of liquid stream (S1) in a flash vessel, compared for example to the pressure of liquid (S1) as obtained in step e), can result in conversion of at least a part of liquid stream (S1) into gaseous phase. Remaining liquid stream (S1) at lowered pressure may be converted into gaseous phase according to step a5) and/or a6).

By lowering the pressure of liquid stream (S1), preferably in a flash vessel, compared to the pressure of liquid stream (S1) obtained in step a), 0 to 80%, preferably less than 10% of liquid stream (S1) may be converted into gaseous phase.

In a further embodiment of the present invention the adsorber (A) to be regenerated in step a) is part of an assembly which contains at least one further adsorber, preferably the at least one further adsorber is under its operation mode during the regeneration of the first adsorber (A) and/or each adsorber within this assembly is identical in respect of the adsorber material and/or its modes of operation.

In step b) an adsorber (A) is regenerated by contact with the stream (S1) obtaining, as the outflow of the adsorber (A), a stream (S2).

Stream (S2)
 i) may comprise at least one alkane and not more than 1000 wt-ppm olefin, preferably not more than 500 wt-ppm olefin, most preferably not more than 100 wt-ppm olefin, preferably the olefin is butane, and/or
 ii) optionally at least one compound containing oxygen and/or sulphur.

Preferably the alkane contains 1 to 14, more preferably 3 to 10, most preferably 4 to 6 carbon atoms in its longest chain.

The at least one alkane can be, for example, linear, branched and/or cyclic and is selected from the group: methane, ethane, propane, butane, pentane, hexane, heptane, octane, nonane and decane. Preferably the at least one alkane is butane.

Step b) may comprise at least one of the component steps b1) to b5):
 b1) heating the adsorber (A) by contact with the gaseous stream (S1), wherein the gaseous stream (S1) is condensed within the adsorber,
 b2) heating the adsorber (A) by contact with the gaseous stream (S1) up to a temperature in the range of 230 to 270° C. without any condensation of the gaseous stream (S1) within the adsorber,
 b3) regeneration of the absorber (A) at a temperature in the range of 230 to 270° C. by contact with the gaseous stream (S1), b4) cooling of the absorber by contact with the gaseous stream (S1) and/or b5) cooling of the absorber (A) by contact with the liquid stream (S1) to a temperature below 80° C., preferably to a temperature in the range of 40 to 60° C., preferably regeneration comprises the component steps b1), followed by b2), followed by b3), followed by b4) and followed by b5).

Condensation, meaning conversion from gaseous into liquid phase, of the components comprised in stream (S1) in step b1), usually takes place if at least one spot, meaning spacial element, inside the adsorber, being the adsorbent and/or the adsorber wall, has a temperature which is below the dew point temperature of the respective components comprised in gaseous stream (S1) present at that spot.

The pressure in the adsorber (A), being in regeneration mode, is defined by the pressure of stream (S1) in the adsorber.

In case step e) and/or a1) (as defined below) are performed, the pressure of stream (S1) in the adsorber (A) is identical or lower as the pressure of stream (S1) as obtained in step e) and/or a1).

In a further embodiment the process according to the present invention comprising at least one, preferably all of the options i) to iii) as follows:

i) the temperature of the gaseous stream (S1) is not more than 100° C., preferably not more than 60° C., higher than the temperature of the adsorber (A), especially during the heating step b1) and/or b2), and/or i) the temperature of the gaseous or optionally liquid stream (S1) is not more than 100° C., preferably not more than 60° C., lower than the temperature of the adsorber, especially during the cooling steps b4) and/or b5), and/or iii) the heating of the adsorber does not exceed 60° C./h, preferably it does not exceed 40° C./h.

Preferably the flow direction of the gaseous stream (S1) through the adsorber (A) in steps b1), b2) and/or b3) is opposite to the flow direction of any organic composition through the same adsorber (A) during its operation mode, and/or the gaseous stream (S1) in step b4) and/or the liquid stream (S1) in step b5) have the same flow direction through the adsorber (A) as the flow direction of any organic composition through the same adsorber (A) during its operation mode.

The organic composition usually comprises at least one olefin, at least one alkane and optionally at least one compound containing oxygen and/or sulphur.

The organic composition comprises preferably at most 80 wt-%, more preferably at most 70 wt-%, most preferably at most 50 wt-% of at least one alkane. Preferably the at least one alkane is butane.

Further, the organic composition comprises preferably at least 19 wt-%, more preferably at least 29 wt-%, most preferably at least 49 wt-% of at least one olefin. Preferably the at least one olefin is butene.

In step c) the stream (S2) is passed through the heat exchange unit (HEU2), wherein the temperature of stream (S2) fed into the heat exchange unit (HEU2) is higher than the temperature of stream (S1) fed into the heat exchange unit (HEU2) in order to transfer heat from stream (S2) to stream (S1).

In a preferred embodiment of the invention i) in step d) the heat exchange unit (HEU1) is an evaporator in order to convert stream (S1) from liquid into gaseous phase and/or in step c) the heat exchange unit (HEU2) is a super-heater in order to superheat stream (S1) and/or ii) stream (S1) is passed in step a) through heat exchange unit (HEU1) prior to (HEU2).

In step d) the stream (S2) is passed through the heat exchange unit (HEU1), wherein the temperature of stream (S2) fed into the heat exchange unit (HEU1) is higher than the temperature of the stream (S1) fed into the heat exchange unit (HEU1) in order to transfer heat from stream (S2) to stream (S1), wherein i) step c) and d) may be run in parallel by splitting stream (S2) into two parts, ii) step c) is followed by step d) and the temperature of stream (S2) fed into the heat exchange unit (HEU2) is higher or equal than its temperature when being fed into heat exchange unit (HEU1) and/or iii) temporarily only one of the steps c) and d) is carried out.

Preferably stream (S2) is passed countercurrently to stream (S1) through the heat exchange unit in step c) and/or step d).

Preferably stream (S2) is cooled/condensed with at least one condenser/and or cooler after being treated according to c) and/or d).

In an optional further step e), carried out prior to step a), stream (S1) is obtained by hydrogenation of a stream (S0) and stream (S0) comprises at least one alkane and at least one olefin in a total of at least 96 wt-%, more preferably in a total of at least 99 wt-%, most preferably in a total of at least 99.5 wt-%.

Stream (S0) may comprise butane and butene, preferably at least 96 wt-% butane and not more than 4 wt-% butene.

The hydrogenation may be carried out by any appropriate method known to the person skilled in the art.

Useful may be a catalyzed hydrogenation using at least a catalyst and a hydrogen source.

Preferably, the catalyst comprises d-block elements, more preferably, for example, Pd, Pt, Ru, Ir, Rh, Cu, Ni or Co, most preferably Pd, Ni, Pt or Rh, in particular preferably Pd or Ni.

The hydrogenation can be performed using $H_2$-gas and/or as catalytic transfer hydrogenation, employing for example ammonium formate, silyl hydrides, $NaBH_4$, cyclohexene or alcohols like methanol and propanol as hydrogen source. Preferably, the hydrogenation is carried out using $H_2$-gas as hydrogen source.

The hydrogen source and the solvent may be identical, for example, in the case of alcohols like methanol.

Any solvent known to the person skilled in the art being appropriate for performing the hydrogenation may be employed.

In general, polar-protic, polar-nonprotic and/or unpolar solvents can be employed, for example methanol, ethanol, propanol, isopropanol, tetrahydrofurane or toluene.

Alternatively, the hydrogenation can be carried out without using any solvent.

In a preferred embodiment, the hydrogenation is carried out without the use of any solvent and with $H_2$-gas as hydrogen source.

Any reactor known to the person skilled in the art being appropriate for performing the hydrogenation may be employed.

Preferably a trickle bed reactor is employed for performing the hydrogenation.

In a further embodiment of the present invention the streams (S1) and/or (S0) originate from an organic composition which has been earlier purified by the same adsorber (A) or by a similar further adsorber during the operation mode of the respective adsorber.

In another embodiment of the present invention an oligomerization of olefins, preferably a dimerization of butene to octene, and/or a distillation step to separate butane from butene is carried out prior to hydrogenation step e) and after the purification of the organic composition employing at least one adsorber in its operation mode.

FIGURES

Figure 2:
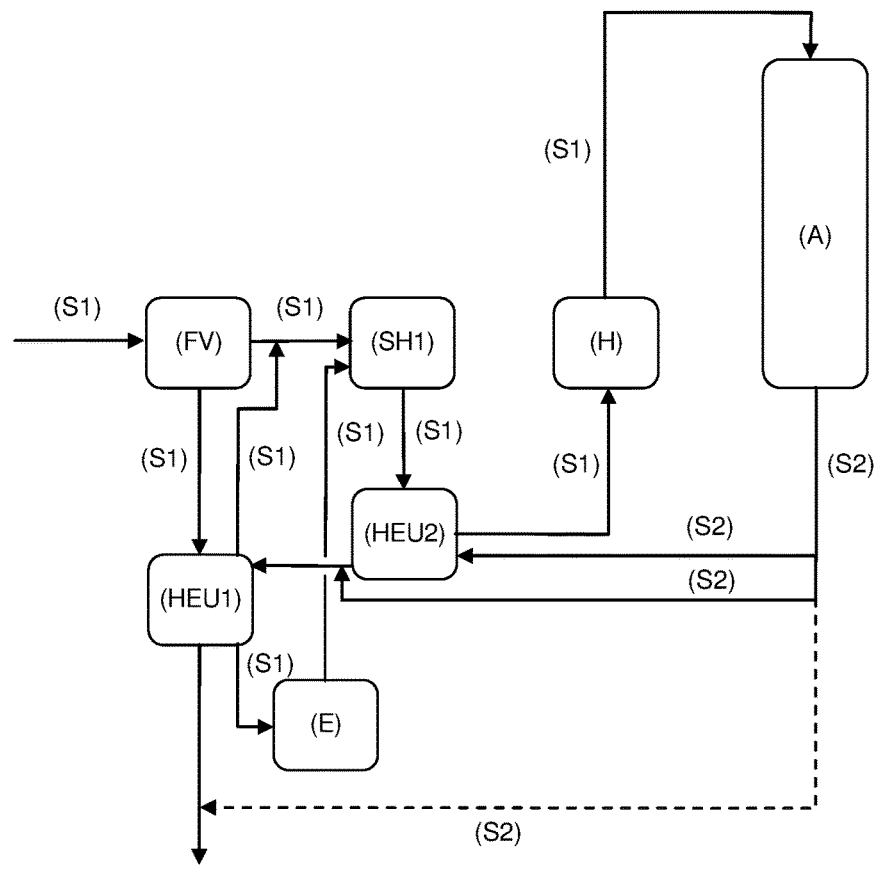

The FIGS. 1 and 2 illustrate certain aspects of the invention. For the sake of clarity not all applicable components and embodiments are drawn in one and/or all figures. Embodiments shown in different figures may be combined with each other and do not exclude the incorporation of further components within the limits of the disclosure of the specification.

FIG. 1 illustrates the most basic assembly of the present invention. Stream (S1) is passed through heat exchange unit (HEU1) followed by heat exchange unit (HEU2). Then stream (S1) as obtained, is fed into an adsorber (A) and the outflow stream (S2) is fed into the heat exchange units (HEU1) and (HEU2) if the temperature of stream (S2) at the respective heat exchange unit (HEU1) and (HEU2) is higher than stream (S1) in order to transfer heat from stream (S2) to stream (S1). The dashed arrow represents a temporarily possible stream (S2), which is not part of the invention.

FIG. 2 demonstrates one further possible embodiment.

Stream (S1) is fed into a flash vessel (FV) and subsequently routed to heat exchange unit (HEU1) and to the super-heater (SH1). From heat exchange unit (HEU1) stream (S1) is passed directly or via evaporator (E) to the super-heater (SH1). Next, stream (S1) is routed to heat exchange unit (HEU2) and via an additional super-heater (H), preferably an electric heater, to an adsorber (A). The outflow stream (S2) of the adsorber (A) is routed to heat exchange unit (HEU1) and (HEU2) according to the basic assembly presented in FIG. 1.

The invention claimed is:

1. A process for regenerating an adsorber (A) comprising:
   a) heating a stream (S1) in at least two heat exchange units (HEU1) and (HEU2);
   b) regenerating an adsorber (A) by contacting the adsorber (A) with the stream (S1) such that a stream (S2) is obtained as an outflow of the adsorber;
   c) passing the stream (S2) through the heat exchange unit (HEU2), wherein the temperature of stream (S2) fed into the heat exchange unit (HEU2) is higher than the temperature of stream (S1) fed into the heat exchange unit (HEU2) such that heat is transferred from the stream (S2) to the stream (S1) in the heat exchange unit (HEU2);
   d) passing the stream (S2) through the heat exchange unit (HEU1), wherein the temperature of stream (S2) fed into the heat exchange unit (HEU1) is higher than the temperature of the stream (S1) fed into the heat exchange unit (HEU1) such that heat is transferred from the stream (S2) to the stream (S1) in the heat exchange unit (HEU1),
   wherein
   i) the passing in c) and d) are optionally carried out in parallel by splitting the stream (S2) into two parts,
   ii) the passing in c) is followed by the passing in d) and the temperature of stream (S2) fed into the heat exchange unit (HEU2) is higher than or equal to the temperature of stream (S2) when being fed into the heat exchange unit (HEU1), or
   iii) temporarily only one of the passings in c) and d) is carried out, and wherein the regenerating in b) comprises at least one of:
   b1) heating the adsorber (A) by contacting the adsorber (A) with the gaseous stream (S1), wherein the gaseous stream (S1) is condensed within the adsorber,
   b2) heating the adsorber (A) by contacting the adsorber (A) with the gaseous stream (S1) up to a temperature in the range of from 230 to 270° C. without any condensation of the gaseous stream (S1) within the adsorber (A),
   b3) regenerating the absorber (A) at a temperature in the range of from 230 to 270° C. by contacting the adsorber (A) with the gaseous stream (S1),
   b4) cooling of the absorber by contacting the adsorber (A) with the gaseous stream (S1), or
   b5) cooling of the absorber (A) by contacting the adsorber (A) with the liquid stream (S1) to a temperature below 80° C.,
   and the heating in b1) is followed by the heating in b2), followed by the regenerating in b3), followed by the cooling in b4) and followed by the cooling in b5), and the heating of the adsorber (A) does not exceed 60° C./h and the temperature of the gaseous stream (S1) is not more than 100° C. and higher than the adsorber (A), and the temperature of the gaseous or liquid stream (S1) is not more than 100° C. and lower than the adsorber.

2. The process according to claim 1, wherein at least one of the heat exchange units (HEU1) and (HEU2) or any further heat exchange unit employed in the process is an evaporator based on heat recovery or a superheater based on heat recovery.

3. The process according to claim 1, wherein
   i) in the passing in d), the heat exchange unit (HEU1) is an evaporator configured to convert the stream (S1) from liquid into gaseous phase, or in the passing in c), the heat exchange unit (HEU2) is a superheater configured to superheat the stream (S1), or
   ii) the stream (S1) is passed in the heating in a) through the heat exchange unit (HEU1) prior to being passed through the heat exchange unit (HEU2).

4. The process according to claim 1, wherein
   i) at least one evaporator is a Kettle-evaporator or a shell-and-tube evaporator, or
   ii) at least one super-heater is a tube bundle heat exchanger,
   iii) the stream (S1) is passed in the heating in a) through at least one superheater (SH1), prior to being passed through the heat exchange unit (HEU2), or
   iv) the stream (S1) is passed in the heating in a) through at least one evaporator, prior to being passed through the heat exchange unit (HEU2), or
   v) the stream (S1) is passed in the heating in a) through at least one further super-heater, after passing the heat exchange unit (HEU2).

5. The process according to claim 1, wherein the stream (S2) is passed countercurrently to the stream (S1) through the heat exchange unit in the passing in c) or the passing in d).

6. The process according to claim 1, wherein the stream (S1)
   comprises at least 99 wt % of at least one alkane, or
   comprises not more than 1000 wt ppm olefin.

7. The process according to claim 1, further comprising, prior to the heating in a):
   e) hydrogenating a stream (S0) such that the stream (S1) is obtained, wherein the stream (S0) comprises at least one alkane and at least one olefin in a total of at least 96 wt %, or the stream (S0) comprises butane and butene.

8. The process according to claim 1, wherein the stream (S2)
- i) comprises at least one alkane and not more than 1000 wt ppm olefin,
- ii) optionally comprises at least one compound containing oxygen or sulphur or
- iii) is cooled, condensed, or cooled and condensed with at least one condenser or cooler after the passing in c) or the passing in d).

9. The process according to claim 1, wherein the heating in a) comprises at least one of:
- a1) feeding a liquid stream (S1) into a flash vessel (FV) to obtain gaseous stream (S1) and liquid stream (S1);
- a2) superheating gaseous stream (S1), optionally obtained in any one or a combination of a1), a3), a4), a5) and a6), in a super-heater (SH1);
- a3) super-heating gaseous stream (S1), optionally obtained in any one or a combination of a1), a2), a4), a5) and a6), in a heat exchange unit (HEU2), which is a super-heater, wherein heat is recovered from the stream (S2);
- a4) super-heating gaseous stream (S1), optionally obtained in any one or a combination of a1), a2), a3), a5) and a6), in a further super-heater (H);
- a5) converting liquid stream (S1), optionally obtained in a1), in a heat exchange unit (HEU1), which is an evaporator, wherein heat is recovered from the stream (S2), into gaseous stream (S1) used in any one or a combination of a2), a3) and a4);
- a6) converting liquid stream (S1), optionally remained from a5), in an evaporator (E), into gaseous stream (S1) and the gaseous stream (S1) obtained is used in any one or a combination of a2), a3), and a4).

10. The process according to claim 1, wherein the flow direction of the gaseous stream (S1) through the adsorber (A) in b1), b2) or b3) is opposite to the flow direction of any organic composition through the adsorber (A) during its operation mode, or the gaseous stream (S1) in b4) or the liquid stream (S1) in b5) have the same flow direction through the adsorber (A) as the flow direction of any organic composition through the adsorber (A) during its operation mode.

11. The process according to claim 1, wherein the stream (S1) originates from an organic composition which has been earlier purified by the adsorber (A) or by a similar further adsorber during the operation mode of the respective adsorber.

12. The process according to claim 7, wherein an oligomerization of olefins, or a distillation process to separate butane from butene is carried out prior to the hydrogenating in e) and after the purification of the organic composition employing at least one adsorber in its operation mode.

13. The process according to claim 1, wherein the adsorber (A) to be regenerated in a) is part of an assembly which contains at least one further adsorber.

14. The process according to claim 13, wherein the at least one further adsorber is under its operation mode during the regeneration of the adsorber (A), or each adsorber within the assembly is identical in terms of the adsorber material or their modes of operation.

15. The process according to claim 6, wherein the stream (S1) comprises at least 99 wt % of butane.

16. The process according to claim 7, wherein the steam (S0) comprises at least 96 wt % of butane and not more than 4 wt % of butene.

17. The process according to claim 9, wherein the heating in a) comprises a1), a2), a3), a4), a5), and a6).

18. The process according to claim 17, wherein the heating in a) comprises at least a2), a3), and a4), and a2), a3), and a4) are conducted in the order of a2), a3), and a4).

19. The process according to claim 12, wherein the oligomerization is a dimerization of butene to octane.

* * * * *